United States Patent [19]

Augustin et al.

[11] Patent Number: 5,192,448

[45] Date of Patent: Mar. 9, 1993

[54] PROCESS FOR BREAKING OIL-IN-WATER EMULSIONS

[75] Inventors: Thomas Augustin, Cologne; Jörg Keldenich, Langenfeld, both of Fed. Rep. of Germany

[73] Assignee: Bayer Aktiengesellschaft, Leverkusen, Fed. Rep. of Germany

[21] Appl. No.: 843,655

[22] Filed: Feb. 28, 1992

[30] Foreign Application Priority Data

Mar. 9, 1991 [DE] Fed. Rep. of Germany ....... 4107643

[51] Int. Cl.$^5$ ............................................. B01D 17/04
[52] U.S. Cl. .................................... 210/708; 210/709; 210/746; 252/328
[58] Field of Search ............... 210/708, 709, 729, 737, 210/739, 745, 746, 96.1, 101; 252/328, 358

[56] References Cited

U.S. PATENT DOCUMENTS

| 3,594,313 | 7/1971 | Carlson | 210/709 |
| 4,444,654 | 4/1984 | Cargle et al. | 210/708 |
| 4,855,061 | 8/1989 | Martin | 210/709 |
| 4,947,885 | 8/1990 | Hart | 252/328 |
| 4,961,858 | 10/1990 | Spei et al. | 210/708 |

FOREIGN PATENT DOCUMENTS 3712106 10/1988 Fed. Rep. of Germany ...... 210/745

*Primary Examiner*—Peter Hruskoci
*Attorney, Agent, or Firm*—Sprung Horn Kramer & Woods

[57] ABSTRACT

Optimum amounts of demulsifiers for breaking oil-in-water emulsions with low salt contents and high surfactant contents are determined by measuring the streaming potential in the emulsion to be broken.

6 Claims, No Drawings

PROCESS FOR BREAKING OIL-IN-WATER EMULSIONS

The present invention relates to a particularly advantageous process for breaking certain oil-in-water emulsions.

In the working and processing of metals, the working-up of used oil, and on other occasions, oil-in-water emulsions with low salt contents and high surfactant contents are obtained. For economic and ecological reasons, such emulsions are worked up by adding one or more demulsifiers to give an aqueous phase of maximum possible purity and an organic phase, the aqueous phase being disposed of via drainage canals, if appropriate after further treatment procedures, and the organic phase being worked up or incinerated, if appropriate also after further treatment procedures.

To achieve good results in the breaking of emulsions, the demulsifier used in each case has to be accurately dosed. An underdose of the demulsifier does not give a pure aqueous phase, i.e. extensively oil-free phase, and/or does not give a pure organic phase, i.e. extensively water-free phase. Although an overdose of the demulsifier often gives a phase separation initially, this is substantially impaired again by re-emulsification.

It has been disclosed hitherto that the hydrocarbon content of aqueous phases can be determined with optical systems (see e.g. U.S. Pat. No. 3,899,688, U.S. Pat. No. 4,128,833, European Published Specification 256 431 and German Offenlegungsschrift 3 712 106). The disadvantage with such optical systems is the sensitivity to contamination of the sensors and detectors to be used, which leads to erroneous measurement results. This method of measurement is therefore unsuitable for determining optimum amounts of demulsifiers for breaking oil-in-water emulsions.

The so-called JAR test is also known for determining optimum amounts of demulsifiers. Here, in series of experiments with the same composition of the emulsion to be broken, and with varying amounts of demulsifier, the amount of demulsifier which gives optimum breaking results is determined by a purely visual method. This visual method also involves a high risk of error because no physical parameter is measured and only visual assessments are made. Moreover, this method is very time-consuming; it cannot be used for a continuous determination of the optimum amount of demulsifier and it is not suitable for adapting the amount of demulsifier to short-term changes in the composition of the emulsion to be broken.

U.S. Pat. No. 4,947,885 has disclosed that in refinery effluents with high salt contents, which contain very small amounts of hydrocarbons and no surfactants, the hydrocarbon content can be determined by measuring the electrical charge of oil droplets in the salt-containing effluents. It was not possible to anticipate that this method could be applicable to other liquid-liquid systems, especially surfactant-containing systems with low salt and high oil contents.

A process has now been found for breaking oil-in-water emulsions with low salt contents and high surfactant contents using demulsifiers, which is characterised in that the optimum amount of demulsifier in each case is determined by measuring the streaming potential in the emulsion to be broken.

In terms of the present invention, emulsions with low salt contents are those containing e.g. less than 3.0% by weight, preferably less than 2.5% by weight, of salts.

In terms of the present invention, emulsions with high surfactant contents are those containing e.g. more than 0.1% by weight, preferably 0.5 to 5.0% by weight, of surfactants. The surfactants can be, for example, anionic, cationic or non-ionic surfactants.

The oil content of the oil-in-water emulsions to be subjected to the process according to the invention can be, for example, 0.5 to 5% by weight and is preferably 0.8 to 2.5% by weight.

Oil-in-water emulsions which can be subjected to the process according to the invention can have a variety of origins. For example, they can be mineral oil-based and partially synthetic cooling lubricant emulsions, rolling oil emulsions, other metal working and processing aids, liquids from the working-up of used oil, oil-containing wash liquors, paintshop effluents, degreasing baths, oil-containing condensates, tank cleaning effluents, bilge waters, slop oils and any other oil-containing effluents.

Any demulsifiers can be used in the process according to the invention. Examples of possible inorganic demulsifiers are salts of divalent and trivalent metals, such as calcium chloride, calcium oxide, aluminium chloride, aluminium sulphate and iron sulphate. Examples of possible organic demulsifiers are polyamines, polyamidoamines, polyimines, polyether-polyamines, quaternised polyamines, quaternised polyamidoamines, homopolymers, copolymers and terpolymers based on acrylic acid and acrylamide, homopolymers, copolymers and terpolymers of diallyldimethylammonium chloride and mixtures of such demulsifiers Such inorganic and organic demulsifiers are known per se.

The essential feature of the present invention is the determination of the optimum amount of demulsifier by measurement of the streaming potential of the emulsion to be broken. One possible procedure is to place a sample of the emulsion to be broken in an apparatus for measuring the streaming potential and then slowly to add the particular desired demulsifier(s), with mixing, until the streaming potential is zero or as close as possible to zero. The amount of demulsifier(s) required for this purpose can then be used to calculate the optimum amount of demulsifier(s) required for the total amount of emulsion to be broken.

Another possible procedure is to pass a sidestream from a relatively large vessel which contains the emulsion to be broken, and to which the particular desired demulsifier(s) are added, through an apparatus for measuring the streaming potential and to stop the addition of demulsifier(s) when the measured potential is zero or as close as possible to zero. This procedure can also be automated.

Finally, it is possible, in the case of continuously produced oil-in-water emulsions, even those of varying composition, continuously to add an optimum amount of demulsifier to the oil-in-water emulsion in the mainstream or a sidestream, by measuring the deviation of the streaming potential from zero and determining the amount of demulsifier required to bring the streaming potential to zero.

The process according to the invention can be carried out at temperatures in the range from 10 to 90° C., for example.

The PCD 02 particle charge detector from Mütek, Herrsching, for example, is suitable for measuring the streaming potential. Said detector is so far known only to be suitable for examining and titrating dispersions, i.e. systems containing solids, or polyelectrolyte solutions.

The process according to the invention has the advantage that it can be used to determine the optimum amount of demulsifiers easily and reproducibly on oil-in-water emulsions on the basis of a physical measurement.

EXAMPLES

EXAMPLE 1

A used cooling lubricant emulsion containing mineral oil, for working metals, which contained less than 1.0% by weight of salt, 1.5% by weight of surfactants and 2.0% by weight of oil, was broken with different organic demulsifiers (in each case as a 1% by weight solution in water). Each demulsifier was measured once by the visual method (JAR test) and once by the process according to the invention with the aid of a PCD 02 particle charge detector from Mütek, Herrsching. The customary integral effluent parameters were then determined in the aqueous phase, affording conclusions on the hydrocarbon content of the aqueous phase and specifically the hydrocarbon content according to DIN 38 409 H18, the COD value according to DIN 38 409 H41 and the TOC value according to DIN 38 409 H3.

The results obtained are shown in Table 1.

TABLE 1

| Demulsifiers (commercial products based on polyamidoamine) | Dosing method a = visually b = according to the invention | Hydrocarbon content (mg/l) | COD value (mg/l) | TOC value (mg/l) |
| --- | --- | --- | --- | --- |
| Type 1 | a | 135 | 11.580 | 3.300 |
|        | b | 120 | 11.800 | 3.340 |
| Type 2 | a | 155 | 10.300 | 3.200 |
|        | b | 30  | 9.850  | 3.190 |
| Type 3 | a | 125 | 11.300 | 3.280 |
|        | b | 10  | 8.500  | 3.175 |
| Type 4 | a | 75  | 10.400 | 3.200 |
|        | b | 25  | 11.200 | 3.270 |
| Type 5 | a | 125 | 10.600 | 3.190 |
|        | b | 20  | 10.200 | 3.140 |

EXAMPLE 2

A used cooling lubricant emulsion containing mineral oil, from a workshop, which had a salt content of less than 1.0% by weight, a surfactant content of 1.0% by weight and an oil content of 1.5% by weight, was broken as described in Example 1 and the aqueous phase was then examined. The results obtained are shown in Table 2.

TABLE 2

| Demulsifiers (commercial products based on polyamidoamine) | Dosing method a = visually b = according to the invention | Hydrocarbon content (mg/l) | COD value (mg/l) | TOC value (mg/l) |
| --- | --- | --- | --- | --- |
| Type 1 | a | 550 | 25.400 | 5.990 |
|        | b | 410 | 15.100 | 4.700 |
| Type 2 | a | 95. | 27.770 | 4.530 |
|        | b | 53  | 14.600 | 4.500 |
| Type 5 | a | 175 | 23.200 | 4.600 |
|        | b | 40  | 14.500 | 4.500 |

What is claimed is:

1. A process for breaking an oil-in-water emulsion having a surfactant content of more than 0.1% weight, a salt content of less than 3.0% weight and an oil content of from 0.5% weight to 5.0% weight, comprising measuring the streaming current potential of the emulsion, determining the amount of demulsifier required to break said emulsion from said measurement and adding the determined amount of demulsifier to break said emulsion.

2. The process of claim 1, in which the emulsion to be broken contains less than 2.5% by weight of salts and 0.5 to 5% by weight of surfactants.

3. The process of claim 1, wherein said emulsion is a continuously produced oil-in-water emulsion, the deviation of the streaming potential from zero is measured, the amount of demulsifier which is required to bring the streaming potential to zero is determined and the optimum amount of demulsifier determined in this way is continuously added to the oil-in-water emulsion.

4. The process of claim 1, which is carried out at temperatures in the range from 10° to 90° C.

5. The process of claim 1, wherein the amount of demulsifier required is determined by placing a sample of said emulsion in an apparatus for measuring the streaming potential of said emulsion, adding said demulsifier with mixing until the streaming potential approaches zero, and determining the amount of demulsifier so used.

6. The process of claim 1, wherein said emulsion is contained within a vessel, a continuous sample stream is withdrawn from said vessel, the streaming current potential of said sample is measured, a predetermined amount of said demulsifier is added to said continuous sample stream, said continuous sample stream is then returned to and mixed with the contents of said vessel and said addition of said demulsifier is continued until said streaming current potential approaches zero.

* * * * *